United States Patent
Gililland et al.

(10) Patent No.: US 12,357,361 B2
(45) Date of Patent: Jul. 15, 2025

(54) KNEE SIZING TOOL AND SYSTEMS AND METHODS FOR USE IN TOTAL KNEE REPLACEMENT PROCEDURE

(71) Applicants: Jeremy M. Gililland, Salt Lake City, UT (US); Daniel B. Prince, Salt Lake City, UT (US)

(72) Inventors: Jeremy M. Gililland, Salt Lake City, UT (US); Daniel B. Prince, Salt Lake City, UT (US)

( * ) Notice: Subject to any disclaimer, the term of this patent is extended or adjusted under 35 U.S.C. 154(b) by 381 days.

(21) Appl. No.: 17/659,413

(22) Filed: Apr. 15, 2022

(65) Prior Publication Data

US 2022/0330995 A1  Oct. 20, 2022

Related U.S. Application Data

(60) Provisional application No. 63/175,262, filed on Apr. 15, 2021.

(51) Int. Cl.
 *A61F 2/46* (2006.01)
 *A61B 17/16* (2006.01)
 *A61B 17/88* (2006.01)
 *A61B 90/00* (2016.01)

(52) U.S. Cl.
 CPC ...... *A61B 17/8805* (2013.01); *A61B 17/1675* (2013.01); *A61B 90/06* (2016.02); *A61B 2090/061* (2016.02)

(58) Field of Classification Search
 CPC ...................................... A61F 2/46–2002/4698
 See application file for complete search history.

(56) References Cited

U.S. PATENT DOCUMENTS

| | | | | |
|---|---|---|---|---|
| 4,973,168 A | * | 11/1990 | Chan | A61B 17/8811 366/139 |
| 5,344,457 A | * | 9/1994 | Pilliar | A61L 27/04 433/175 |
| 6,294,187 B1 | * | 9/2001 | Boyce | A61L 27/3645 424/484 |
| 6,361,731 B1 | * | 3/2002 | Smith | B29C 33/405 264/318 |
| 6,440,444 B2 | * | 8/2002 | Boyce | A61L 27/3691 424/443 |
| 6,905,516 B1 | * | 6/2005 | Lemaitre | A61F 2/28 623/23.62 |
| 7,087,082 B2 | * | 8/2006 | Paul | A61F 2/28 623/925 |
| 9,895,830 B2 | * | 2/2018 | Vogt | B29C 39/003 |
| 10,492,914 B2 | * | 12/2019 | Magagnoli | B29C 45/0013 |
| 10,993,810 B2 | * | 5/2021 | Magagnoli | B22F 5/00 |
| 2002/0055783 A1 | * | 5/2002 | Tallarida | A61B 17/1764 623/20.14 |
| 2006/0051395 A1 | * | 3/2006 | Beyer, Jr. | A61P 19/00 514/21.3 |
| 2012/0032374 A1 | * | 2/2012 | Bratt | B28B 7/241 264/328.2 |

(Continued)

*Primary Examiner* — Zade Coley
(74) *Attorney, Agent, or Firm* — Workman Nydegger

(57) ABSTRACT

A diameter sizing tool for use in reversion of total knee arthroplasty, the diameter sizing tool including a body having an upper surface, a lower surface, and a peripheral edge, a central cutout disposed through the body from the upper surface to the lower surface, and a plurality of sizing through-holes circumferentially disposed in the body and radially towards the peripheral edge.

17 Claims, 16 Drawing Sheets

(56) References Cited

U.S. PATENT DOCUMENTS

2016/0129610 A1* 5/2016 Cappelletti ........... A61F 2/3094
                                                   249/61
2016/0235537 A1* 8/2016 Magagnoli ................ A61F 2/40
2017/0071745 A1* 3/2017 Magagnoli ................ B22F 5/00

* cited by examiner

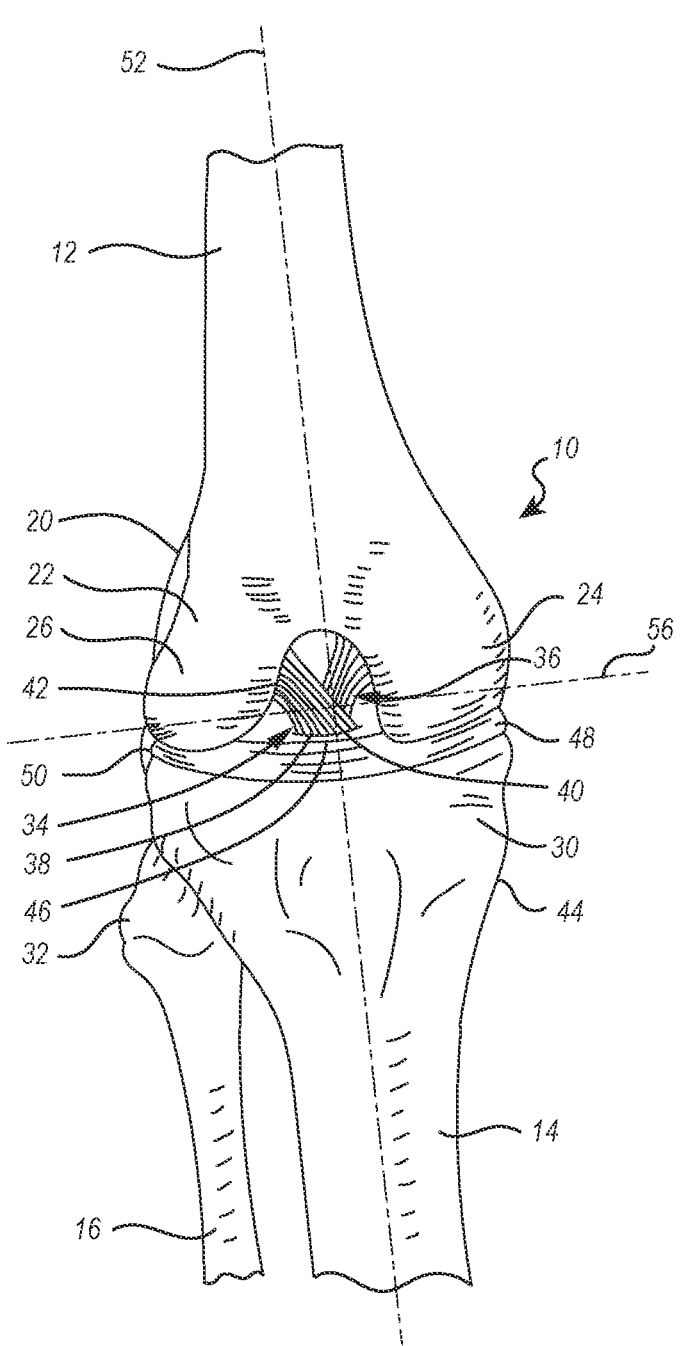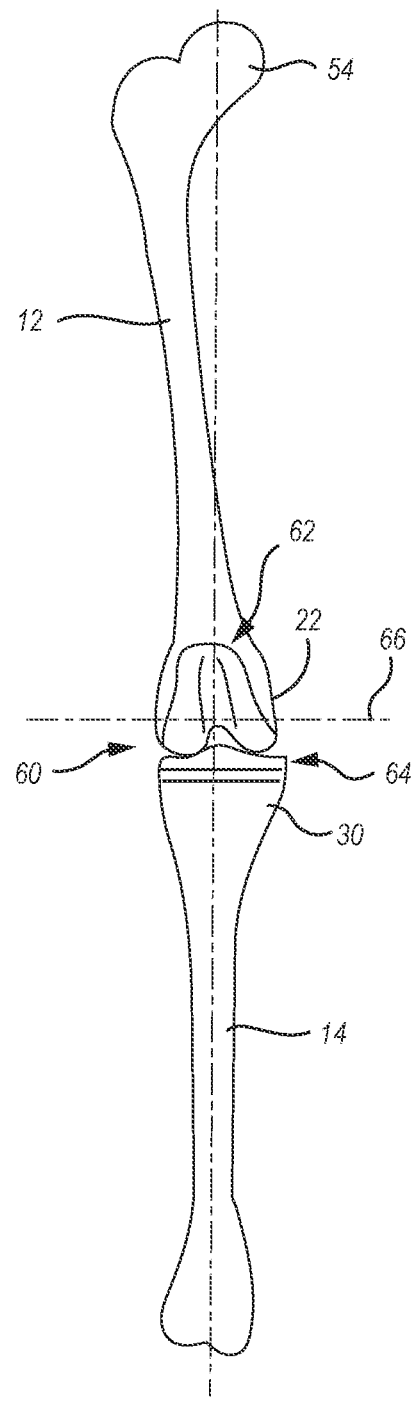
FIG. 1
FIG. 2

KNEE SIZING TOOL AND SYSTEMS AND METHODS FOR USE IN TOTAL KNEE REPLACEMENT PROCEDURE

This application is a non-provisional of, and claims priority to, U.S. Provisional Patent Application No. 63/175,262, filed Apr. 15, 2021, the entire specification of which is incorporated herein in its entirety.

BACKGROUND OF THE INVENTION

1. The Field of the Invention

The present disclosure relates generally systems, apparatuses and methods for total knee replacement, such as a knee sizing tool for use in a total knee replacement procedure.

2. The Relevant Technology

Total joint arthroplasties of the hip and knee are of the most common surgical procedures performed today. Recent reports measuring patient-reported outcomes support improved quality of life after these procedures. The success of primary total joint arthroplasties in an aging population has led to increased arthroplasty utilization.

However, in some circumstances, a revision of a previous total joint arthroplasty is necessary. The current standard of care in the United States is a two-stage revision. The first stage of the revision has historically used a static spacer consisting of a block of antibiotic-impregnated cement. Over time, the routine use of static spacers has diminished in favor of articulating spacers that allow a range of motion. Several studies have shown similar rates of eradication of infection between static and articulating spacers, while the latter provides easier surgical approaches and a trend toward a better range of motion after the second stage.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 1 is an anatomical view of a human knee joint having an anterior cruciate ligament and posterior cruciate ligament;

FIG. 2 is a diagram of a total prosthetic knee implant, implanted at the joint between a human femur and tibia, prior to complete synovectomy and replacement with another total prosthetic knee implant according to the present invention.

DETAILED DESCRIPTION OF THE INVENTION

Figure 3:
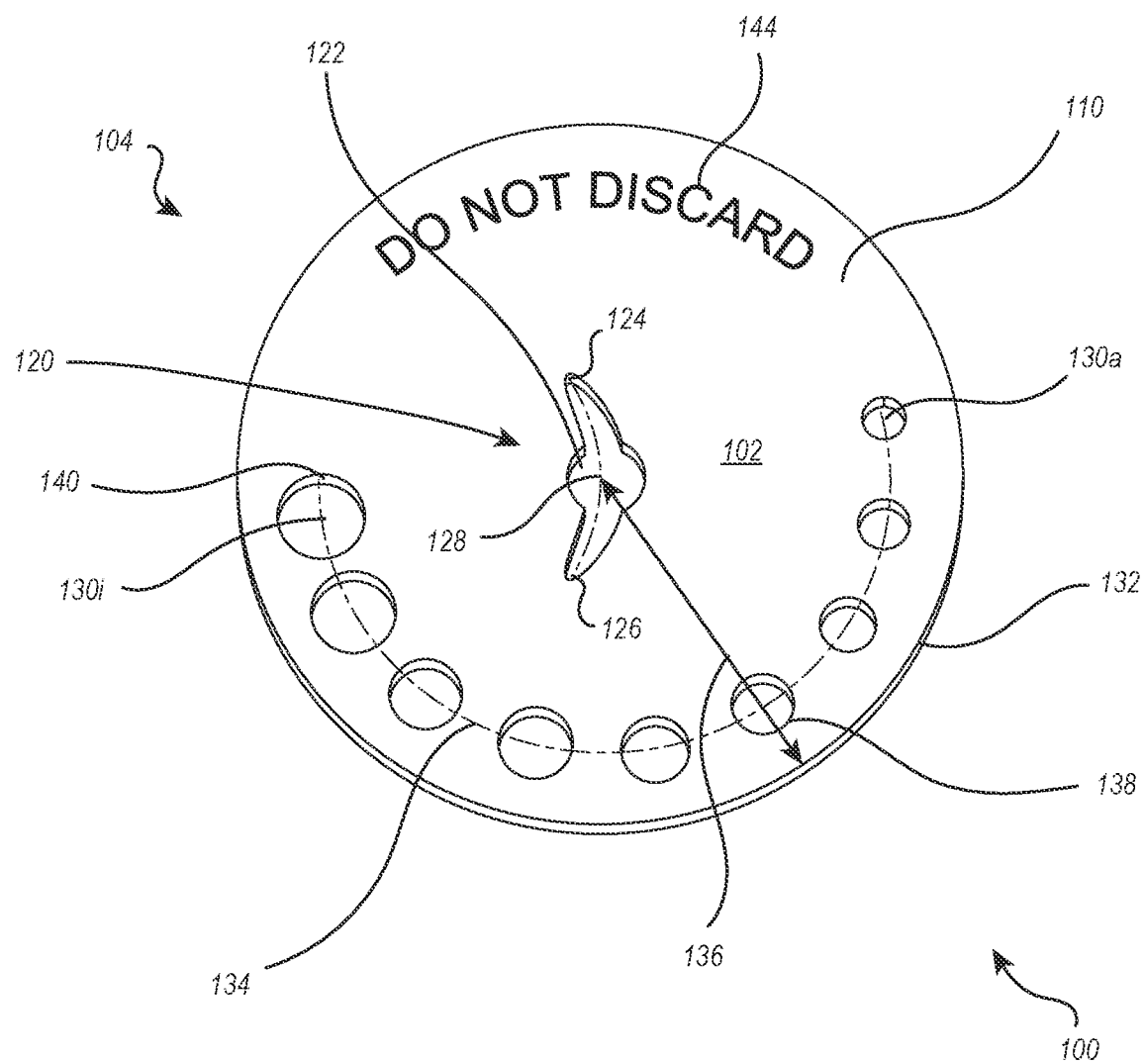
FIG. 3 illustrates a diameter sizing tool according to the present invention.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to systems, methods, and devices associated with revision of a total knee arthroplasty. The systems, methods, and devices can provide a reusable sizing tool or block to aid with determining tibial buildup and sizing of femoral and/or tibial dowel diameters in a simple and effective manner. Thereby resulting in higher accuracy with tibial buildup and dowel diameters. The systems, methods, and devices of the present invention can be used in total knee arthroplasty revision to achieve implantation of a balanced, stable, and reasonably durable articulating antibiotic spacer (a femoral component and a tibial component) that can provide patients with a well-functioning knee with the freedom of full weightbearing and activity.

While the present disclosure will describe a particular implementation of apparatuses and systems, with associated methods, for revision of a total knee arthroplasty, it should be understood that any of systems, apparatuses, and methods described herein may be applicable to other uses. Additionally, elements described in relation to any embodiment depicted and/or described herein may be combinable with elements described in relation to any other embodiment depicted and/or described herein.

FIG. 1 shows a patient's natural knee joint 10 prior to the surgical procedure. Illustrated are different portions of the femur 12, the tibia 14, and the fibula 16. The femur 12 has an exterior surface 20, with a lower portion 22 having a medial condyle 24 and lateral condyle 26. An upper portion 30 of the tibia 14 and an upper portion 32 of the fibula 16 are also illustrated.

One end 38 of an anterior cruciate ligament 34 is attached to an anterior portion of an intercondylar eminence 40 of the tibia 14, and a second end 42 of the anterior cruciate ligament 34 is attached to a posterior portion of the medial aspect of the lateral femoral condyle 26. The posterior cruciate ligament 36 passes upwardly and forward on the medial side of the anterior cruciate ligament 34, extending from behind the intercondylar eminence 40 to the lateral side of the medial condyle 24 of the femur 12. An exterior surface 44 of the tibia 14, a tibial plateau 46, a medial meniscal cartilage 48 and a lateral meniscal cartilage 28 is also illustrated.

The femur 12 and tibia 14 extend along a mechanical axis 52 which is generally parallel to the tibia 14 and passes through a head 54 of a natural hip joint (not shown). The tibia 14 rotates about an axis 56 relative to the lower portion 22 of the femur 12 that bisects the condyles 24 and 26 and is generally perpendicular to the mechanical axis 52. Axis 56 corresponds with what is referred to in the medical industry as the "knee joint line," this joint line being separated into a medial joint line portion which is the portion of the joint line starting at the intersection of the axis 52 and axis 56 and extending to the right (i.e., in the medial direction) of the knee joint, and a lateral joint line which is the portion of the line starting at the intersection of the axis 56 and axis 52 and extending to the left (i.e., in the lateral direction) of the knee joint. During articulation of the knee joint 10 between flexion and extension, the medial condyle 24 engages the tibia 14 along a medial bearing surface bordered by the medial meniscal cartilage 48, while the lateral condyle 26 engages the tibia 14 along a lateral bearing surface bordered by the lateral meniscal cartilage 50. The anterior crucial ligament 34 limits forward movement of the tibia 14 under the femoral condyles 24 and 26, while the posterior cruciate ligament 36 limits backward movement of the tibia 14 under the femoral condyles 24 and 26.

Referring now to FIG. 2, the natural knee joint 10 has been replaced by a first prosthetic knee implant 60 that will be removed because of an infection, for instance, according to the present invention. The prosthetic knee implant 60 includes a femoral component 62 affixed to the lower portion 22 of the femur 12 and a tibial component 64 affixed to the upper portion 30 of the tibia 14. The femoral component 62 includes a tibial axis of rotation 66 relative to the lower portion 18 of the femur 12 that is generally perpendicular to the mechanical axis 52 and is also oriented in substantial similarity to axis 56 of FIG. 1.

Turning to FIG. 3 illustrated is a diameter sizing tool or diameter sizer 100, such as a spacer block, that can be used during a revision procedure, for instance, when revision of previous total knee arthroplasty (TKA) is to be performed to remove and replace femoral and tibial components because of infection, misalignment, etc. During a first TKA, a gap-balanced technique can be used where tension and flexion gaps are balanced before femoral bone cuts are made, with ligaments being released before the cuts are made to achieve the desired tension and flexion gaps. Following gap balancing the femoral and tibial cuts can be performed, with high accuracy of the tibial cuts being desired to avoid malrotation of the femoral component. As such, determining the correct depth and alignment on coronal and sagittal planes is important to effectiveness of the TKA.

During a revision procedure, such as a revision procedure using gap-balancing technique, a diameter sizing tool can be used to determine the appropriate tibial buildup for the tibia component. It can also be used to determine the approximate size for a femoral dowel. The diameter sizing tool 100 of FIG. 3 is illustrative of such a tool.

Figure 3A:
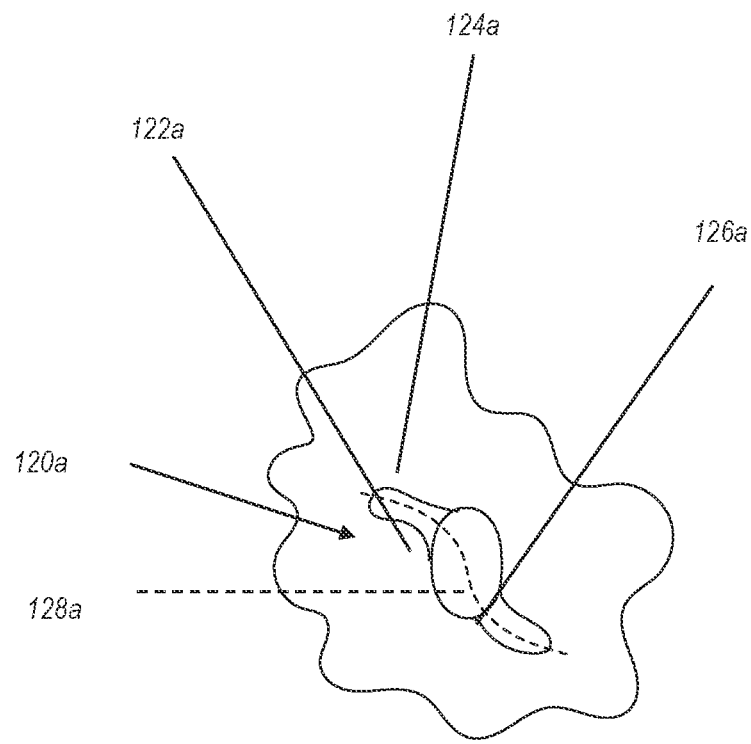
FIG. 3A illustrates an alternate diameter sizing tool according to the present invention.
Figure 3B:
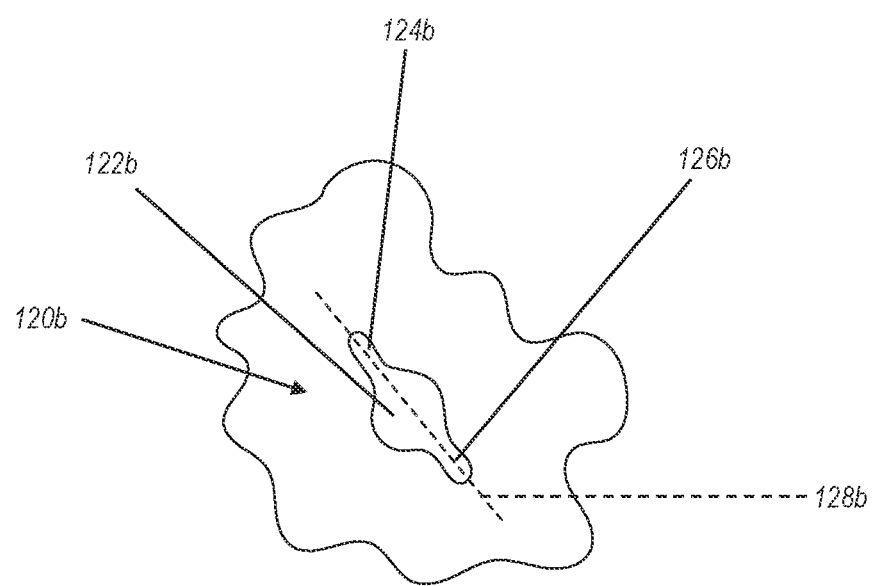
FIG. 3B illustrates an alternate diameter sizing tool according to the present invention.

The diameter sizing tool 100 has a generally circular block body 110 with a central cutout 120 and a plurality of through holes 130 radially disposed from the central cutout 120. The central opening 120 can selectively receive a tibial keel of a tibial component so that the diameter sizing tool 100 can be used to flatten and optionally smooth the cement needed to achieve the desired gap thickness, such as an extension gap and a flexion gap. In the illustrated configuration, the central cutout 120 includes a central opening 122 with a first opening extension 124 and a second opening extension 126. The central opening 122 approximates a central portion of the tibial keel, while the first opening extension 124 and the second opening extension 126 accommodate the keel supports, as will be discussed in more detail hereinafter. The first opening extension 124 and the second opening extension 126 curve away from the central opening 122 along an arc 128. While reference is made to the central cutout 120 including the central opening 122, the first opening extension 124, and the second opening extension 126, it will be understood that the central cutout 120 can have other configurations to accommodate different keel configurations. For instance, instead of extending to curve along the arc 128, the first opening extension 124 and the second extension 126 could curve in opposite directions, as illustrated in FIG. 3A, or need not curve, but extend away from the central opening 122 linearly as illustrated in FIG. 3B.

The plurality of through holes 130 are disposed about the central cutout 120. The through holes 130 can be used to approximate particular dimension of femoral and tibial dowels that are to be used during revision. For instance, during revision the tibial and femoral canals are reamed and the final diameters of both the tibial and femoral canals are identified. While the diameter of the canals can be sized based upon the reamers used to form the canals, the through-holes 130 can optionally be used to approximate the canal diameters, such as by comparing one or more of the through holes 130 of the diameter sizing tool 100 with the reamed canals to approximate the size of the tibial and femoral canals. The clinician can rotate body block 110 to align the through holes 130 above the canal opening to approximate the canal opening diameter.

With tibial and femoral canal dimensions identified, cement dowels can be formed by wrapping antibiotic cement or buildup cement about a central rod of the tibial component, for instance, or rolling the antibiotic cement into an elongate cylindrical shaped member for insertion into the femoral canal. To aid with obtaining the desired diameters, the dowel, either the antibiotic cement alone or the combination of antibiotic cement and central rod, such as a Steinman pin, can be passed through one or more of the through holes 130 to accurately size the dowel's diameter. With the plurality of through holes 130 increasing in diameter from 130a to 130i in a circumferential direction about a peripheral edge 132 of the diameter sizing tool 100, the clinician can select the specific through hole for the desired dowel. The holes 130a-130i can follow an arc 134 that positions an axis of each hole an equal distance from the peripheral edge 132. Alternatively, the arc 134 can be spaced from the peripheral edge 132 so that an edge 138 of each hole 130a-130i that intersects radii 136 extending from the central opening 122 to the peripheral edge 132 through each hole 130a-130i is at the same distance from the peripheral edge 132.

While nine through holes 130 are illustrated it would be understood that a greater or fewer number of through holes 130 is also possible. For instance, the number of through holes 130 can range from about 0 to about 20, from about 1 to about 15, from about 2 to about 10, from about 3 to about 9, or other number of holes.

Each through hole 130 includes an interior wall 140. Each wall 140 is perpendicular to an upper surface 102 of the spacer body 100. Optionally, a junction between the wall 140 and the upper surface 102 can include a chamfer or curved profile to transition between the wall 140 and the upper surface 102.

In addition to aiding with the dimensions of the dowel, and optionally the sizes of the tibial and femoral canals, the planar orientation of an upper surface 102 and a lower surface 104 of the diameter sizing tool 100 can be used to flatten and smooth the buildup cement of the tibial component. For instance, a clinician can slide the diameter sizing tool 100 along the dowel and/or a central rod, such as a Steinman pin, until the diameter sizing tool 100 contacts the buildup cement and move the diameter sizing tool 100 towards an end of the tibial component to flatten and smooth the buildup cement. Excess cement can pass through the through holes 130 and out from the sides of the diameter sizing tool 100 and removed.

Disposed in one or both of the upper surface 102 and the lower surface 104 are indicia 144 that provide information to the clinician about the holes 130, for instance. As illustrated the indicia 144 provide a diameter of each hole 130 to allow the clinician to approximate the femoral and tibial canals. For instance, the diameters of the holes 130 can range from about 10 mm to about 18 mm, from about 5 mm to about 30 mm, from about 6 mm to about 25 mm, or other ranges, with the indicia 144 providing a visual indication of those dimensions on the diameter sizing tool 100. Additionally, a diameter difference between adjacent holes 130 of the plurality of holes 130 can be about 0.25 mm to about 1.5 mm, 0.5 mm to about 1 mm, or about 1 mm.

Generally, the diameter sizing tool 100 can be fabricated from a polymer material. More generally, the diameter sizing tool 100 can be fabricated from a polymer, a metal, an alloy, a composite, combinations and/or modifications thereof.

Figure 4:
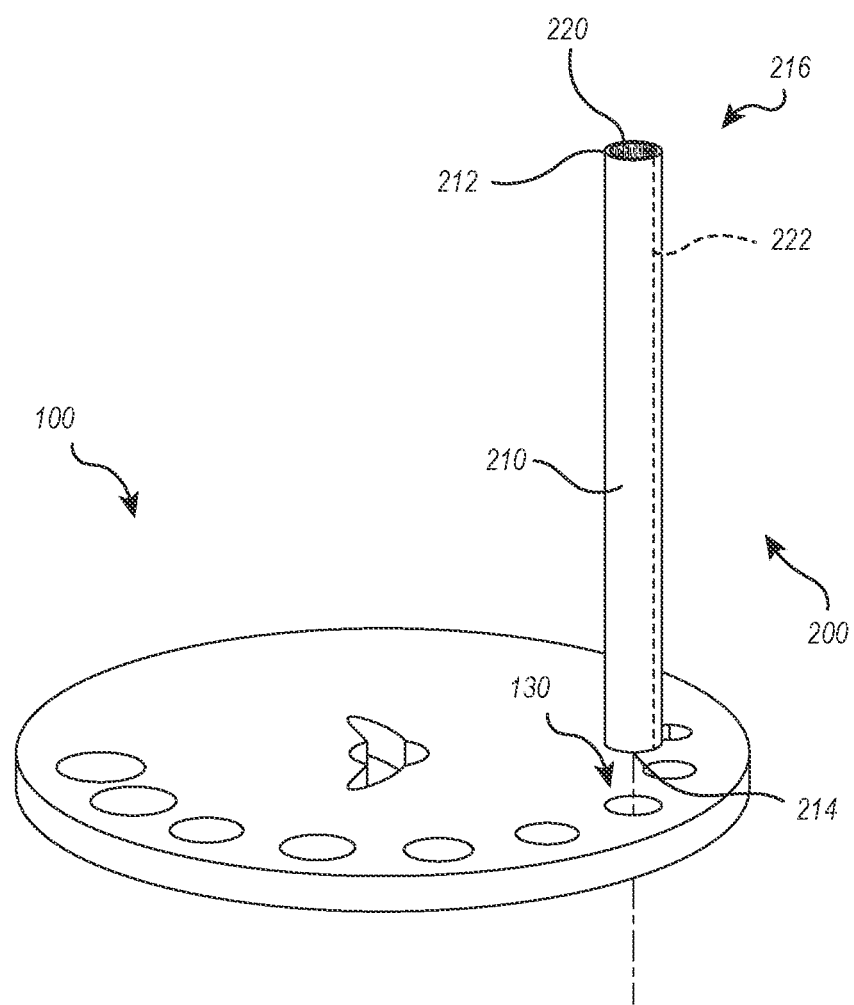
FIG. 4 illustrates another alternate diameter sizing tool according to the present invention.

In addition to, or as an alternate to the diameter sizing tool 100 of FIG. 3, a clinician can use diameter sizing tool 200 as illustrated in FIG. 4. The diameter sizing tool 200 has an elongate body 210 that can be used to form a femoral dowel or a tibial dowel portion of a tibial component, for instance, in a simple manner so that an appropriate fit is achieved between the femoral dowel and the femoral canal and the dowel portion of the tibial component and the tibial canal. The elongate body 210 with a first end 212 and a second end 214 with a lumen 216 extending from the first end 212 to the second end 212.

The lumen 216 can be filled with the buildup cement and act as a form to shape the femoral dowel or the tibial dowel portion. The lumen 216 can be filled by, for example, injecting, poring, or otherwise depositing cement into the lumen 216, with the elongate body 210 supporting and shaping the buildup cement while it cures, sets, or otherwise solidifies. In the case of the tibial component, and as will be described in more detail hereinafter, a securing pin can be received within the lumen 216 prior to or following filling with the buildup cement. With the securing pin in place, the elongate body 210 supports and shapes the buildup cement around the securing ping while the cement cures, sets, or otherwise solidifies.

During filling, or during the time when the buildup cement is setting, curing, or solidifying, the diameter sizing tool 100 can optionally be used as a support for the diameter sizing tool 200, as illustrated in FIG. 4. The first end 212 or second end 214 of the elongate body 210 can be received within one of the through holes 130 so that the diameter sizing tool 100 acts as a base or support to position the elongate body 210 of the diameter sizing tool 200 in a generally vertical orientation. The diameter sizing tool 100 can rest on a table or other surface with the elongate body 210, or diameter sizing tool 200, extending from the diameter sizing tool 100. In the case of tibial component dowel formation, the tibial component can be positioned at one end of the elongate body 210, or the diameter sizing tool 200, and the diameter sizing tool 100 at the other.

Once the buildup cement has cured, set, or otherwise solidified, the elongate body 210 can be removed from the buildup cement. The elongate body 210 can be cut and removed. The elongate body 210 can optionally include a coating 220, such as TEFLON or other coating to aid with removal of the buildup cement from within the lumen 216 to aid with removal. For instance, the coating 220 provides lubriciousness to allow sliding and releasing of the elongate body 210 from the buildup cement, such as by rotating and sliding the elongate body 210 from the buildup cement, by pushing the buildup cement (whether alone in the form of a femoral component or in the form of a tibial component) from within the elongate body 210 using a pushing member (not shown), a combination of rotating, sliding, and pushing the buildup cement, or some other manner. Alternatively, the material forming the elongate body 210 itself can allow the sliding and releasing of the elongate body 210. In another configuration, the elongate body 210 includes a preferential cut region 220 having perforations, holes, or a thinned area along which the elongate body 210 can either tear or separate.

Figure 21:
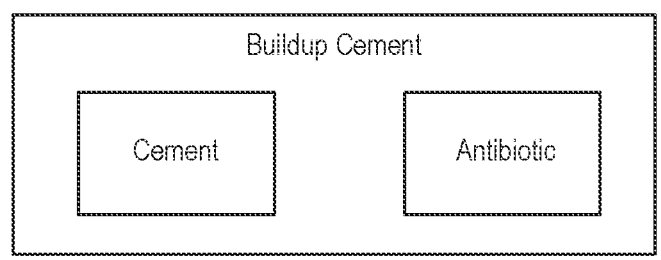
FIG. 21 illustrates a kit for forming the buildup structure of a femoral component, a femoral dowel, and a tibial component.
Figure 21:
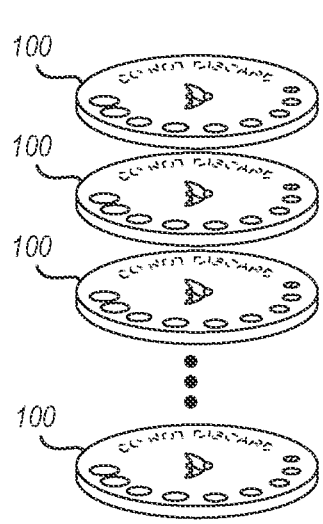
Figure 21:
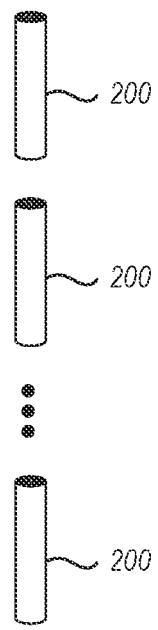

The specific configuration of the elongate body 210 can be selected based upon the reamed diameter of the tibial canal, for instance. In such a case, the elongate body 210 can form part of a kit, such as kit 300 of FIG. 21, having buildup cement and a number of differently sized diameter sizing tools each having a lumen with a different diameter. For instance, the inside diameter of the lumens 216 can range from about 10 mm to about 18 mm, from about 5 mm to about 30 mm, from about 6 mm to about 25 mm, or other ranges. The clinician can select the particular elongate body 210 based upon the desired outside diameter of the femoral dowel or tibial dowel portion. It will be understood that the kit 300 can also include one or more of the various diameter sizing tools 100, 200 in addition to including the buildup cement used to form the femoral dowel and/or the tibial dowel portion.

The elongate body 210, and so the diameter sizing tool 200, can be formed of silicone, polymer, metal, alloy, composite, or combinations or modifications thereof. The material is selected so there is little, if any, expansion of the elongate body 210 upon injection or pouring of the buildup cement within the lumen 216. This maintains the accuracy of the inside diameter of the lumen 216 and so the accuracy of the outside diameter of the dowels.

Turning to FIGS. 5-20, described is one method of using the diameter sizing tool 100 during a revision procedure. While reference is made to one particular method, it will be understood that other methods can be performed with the diameter sizing tool 100, whether or not those methods are performed as part of a revision.

Figure 5:
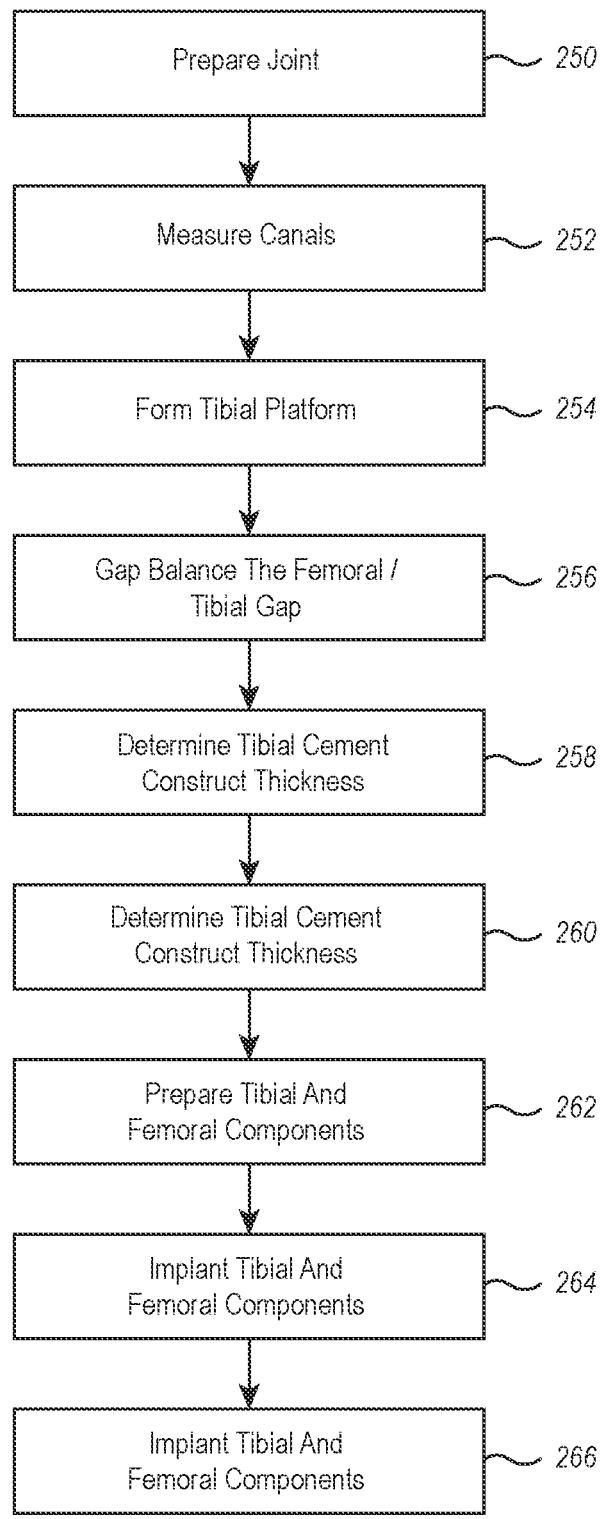
FIG. 5 illustrates a method of performing a total knee arthroplasty according to the presentation invention.
Figure 6:
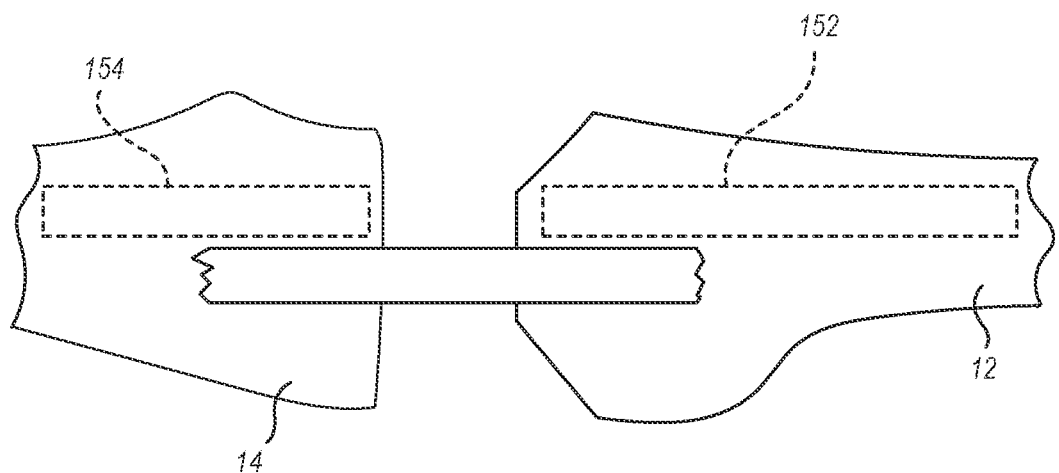
FIG. 6 is a side view of a partially prepare knee joint as part of a total knee arthroplasty.

As illustrated in FIGS. 5-20, as in all infected cases, a revision procedure can begin with preparing the joint, such as act 250 (FIG. 5). This can include a complete synovectomy, restoration of the medial and lateral gutters, and implant removal, such as removal of femoral component 62 and tibial component 64 (FIG. 2). During joint preparation, attempts are made to spare as much host bone as possible, but a thorough debridement of all contaminated tissues is imperative for success of the TKA. As part of the debridement, the femoral and tibial canals 152, 154 are reamed, such as using an orthopedic reamer. Thereafter, the final diameters of both the femoral and tibial canals 152, 154 are identified, such as act 252 (FIG. 5). The final diameters can be calculated based upon the particular reamer used to form them. Alternatively, the diameter sizing tool 100 can be used by approximating the femoral and tibial canals 152, 154 by aligning one or more of the holes 130 with the opening of the femoral and tibial canals 152, 154.

Figure 7:
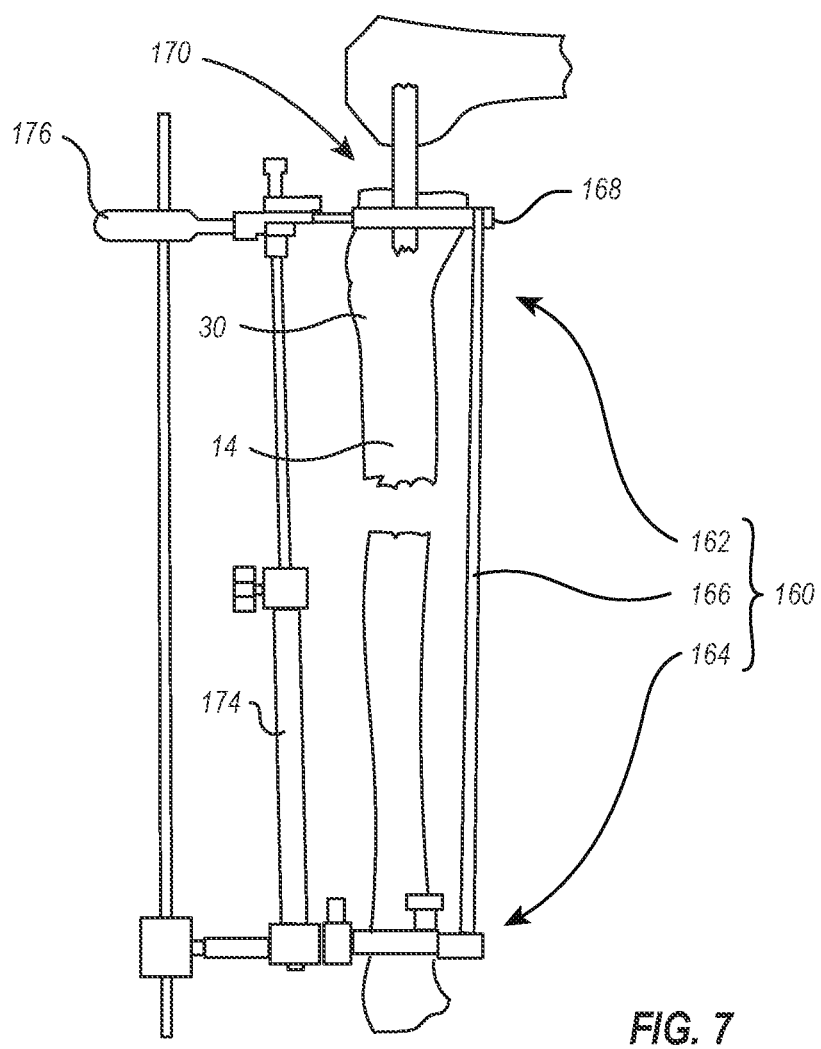
FIG. 7 is a side view of a tibial jig attached to the tibia as part of a total knee arthroplasty.

With the tibial and femoral canals 152, 154 determined, a stable tibial platform is formed, such as act 254 (FIG. 5). With the knee maximumly flexed, as illustrated in FIG. 7, a jig 160 having a proximal jig 162 and a distal jig 164 connected by a rod 166. The jig 160 can be mounted to determine cut depth and provide a guide for cutting the tibia to form the tibial platform 170, as illustrated in FIG. 7. The jig 160 can be an extramedullary tibial cutting jig that is not affected by bowing of the tibial diaphysis. The jig 160, can be, for example, a jig typically associated with a primary TKA rather than a revision TKA.

The proximal jig 162 is positioned towards an upper end 30 of the tibia 14, with the distal alignment jig 164 mounted towards a lower end of the tibia 14 near the ankle. The proximal jig 162 and the distal jig 164 are centered or aligned with the shaft of the tibia 14 so that the proximal jig 162 is aligned with the anatomical mechanical axis of the tibia 14 so the guide 168 provides for forming a cut perpendicular to the mechanical axis. For instance, the proximal jig 160 can be positioned so that a guide 168 of the proximal jig 160 fits or conforms to the anterior cortex of the tibia. With the guide 168 in place, such as by pining the guide 168 to the tibia 14, and depth of resection cut determined using a stylus or other depth measuring device, the guide 168 can be used to remove approximately about 0.5 mm to about 10 mm, about 1 mm to about 5 mm, or about 1 mm to about 2 mm of bone using an oscillating saw or other saw or cutting tool. This restores the bony platform that is perpendicular to the mechanical axis of the tibia 14, and so form the tibial plateau 170.

Figure 8:
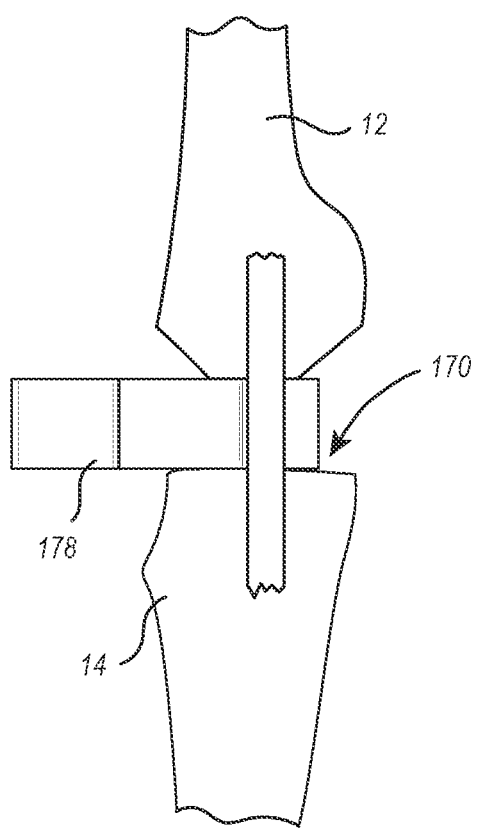
FIG. 8 is a side view of a lollipop spacer used as part of a total knee arthroplasty.

To confirm the accuracy of the tibial plateau 170, a drop rod 174 can be positioned through a drop rod adapter 176 associated with the guide 168, and the tibia resized, as needed, based upon sizing for approximate fit with the femur 12 using a lollipop sizer 178 disposed between the tibial plateau 170 and the femur 12, as illustrated in FIG. 8. This is an approximate fit because the femur 12 still needs to be resized or positioned in preparation for or as part of gap-balancing.

Once the approximate fit is determined, the distal femoral cut is restored, such as act 256 (FIG. 5). An intramedullary rod 180 is placed in the femoral canal 154, and a distal femoral cutting jig 182 is set at the angle between the femoral anatomic and mechanical axes along the intramedullary rod 180 and then pinned to the femur 12. The axes can be templated from preoperative long-standing films, such that the axes are about 5 degrees to about 6 degrees. A resection depth is set using the distal femoral cutting jig 182, such that the resection depth is about 0.5 mm to about 10 mm, about 1 mm to about 5 mm, or about 1 mm to about 2 mm of bone.

Figure 9:
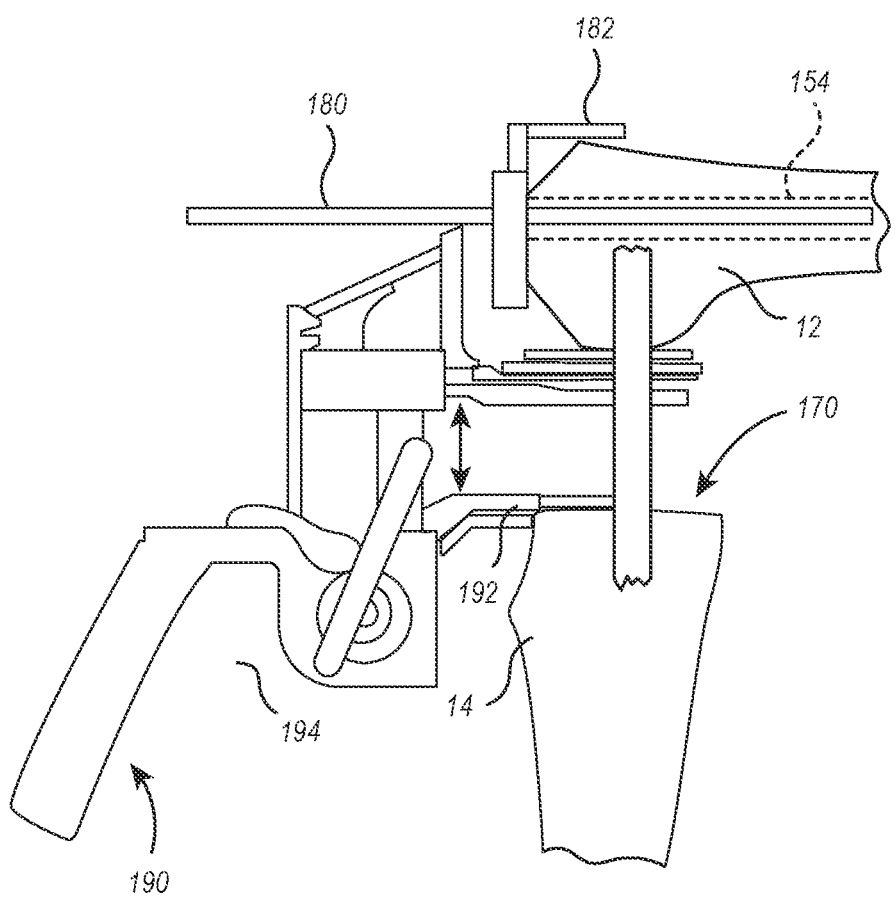
FIG. 9 is a side view of a femoral jig attached to the femur as part of a total knee arthroplasty.

Before cutting the femoral bone using an oscillating saw, and as illustrated in FIG. 9, paddles 192 of a balancing device 190 are slid onto the distal femoral bony surfaces. Any large bony defects on the medial or lateral side where the paddles 192 do not come into contact with the bone will be addressed using differential distal femoral augments to make up for bone loss. A cleanup cut is then performed on the distal femur to provide a flat bony surface at the appropriate distal femoral valgus angle Thereafter, the distal femoral cutting jig 182 can be removed and scarred and adhered posterior capsule can be released. The posterior condyles are also examined, and where necessary, a rongeur can be used to remove any remaining osteophytes to establish reliable posterior condylar surfaces on which paddles 192 can rest. In some circumstances, instead of using a rongeur, an oscillating saw or other medical instruction can be used to flatten the posterior condyle cuts.

Figure 10:
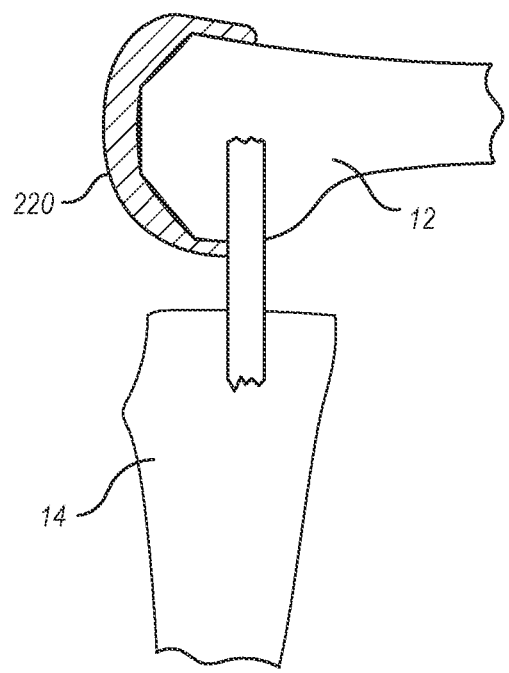
FIG. 10 is a side view of a trial cruciate-retaining (CR) femoral component mounted to the femur as part of a total knee arthroplasty.
Figure 11:
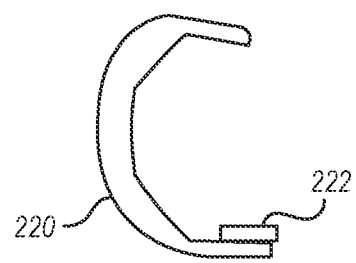
FIG. 11 is a side view of a trial cruciate-retaining (CR) femoral component.

With the femoral surfaces prepared, a trial cruciate-retaining (CR) femoral component 220 can be used to approximate the final femoral component, such as illustrated in FIGS. 10 and 11. When any large bony defects on the medial or lateral side where the paddles 192 did not come into contact with the bone were identified earlier, then magnetic augments 222 of an appropriate size are placed on the trial CR femoral component 220, such as illustrated in FIGS. 10-11. The magnetic augments 222 can range in thickness from about 1 mm to about 15 mm, about 1 mm to about 10 mm, about 2 mm to about 8 mm, or about 3 mm to about 5 mm.

Figure 12:
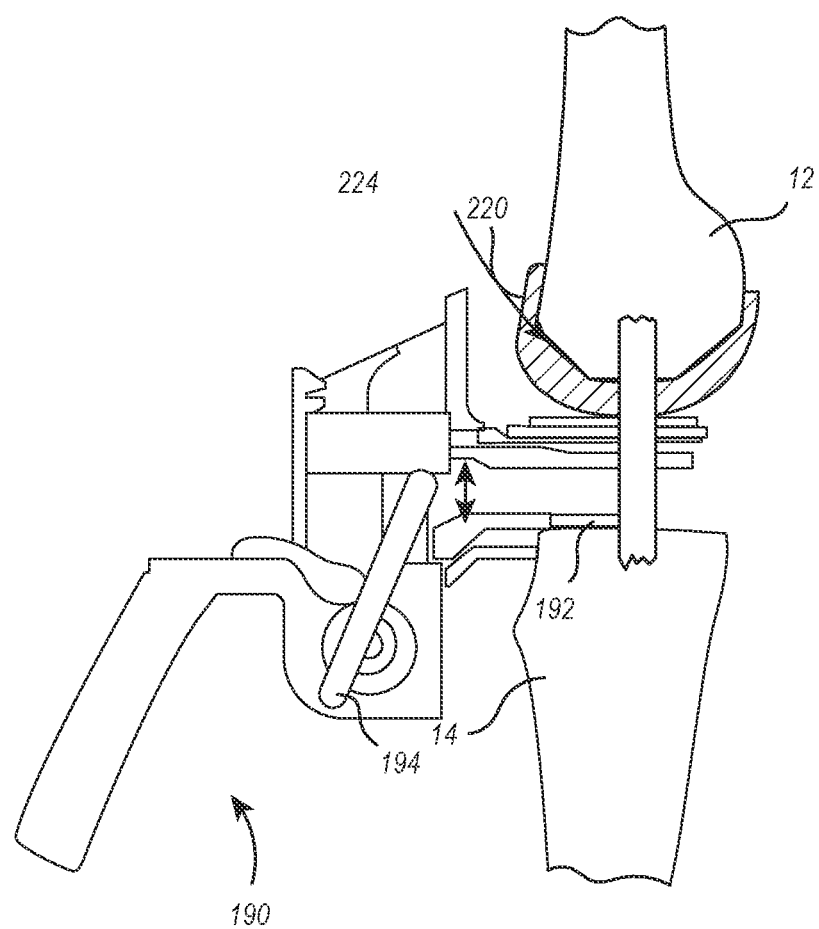
FIG. 12 is a side view of a gap-balancer being used to measure an extension gap of the joint as part of a total knee arthroplasty.
Figure 13:
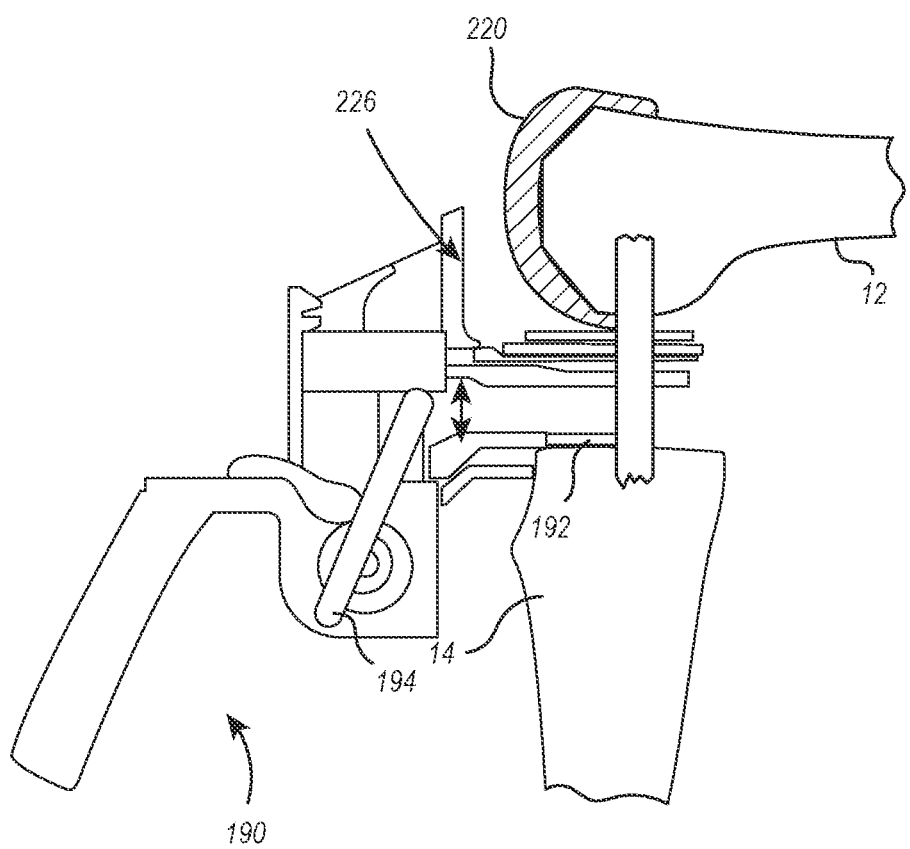
FIG. 13 is a side view of a gap-balancer being used to measure a flexion gap of the joint as part of a total knee arthroplasty.

With the femoral surfaces prepared and a trial CR femoral component 220 selected, with the optional magnetic augments 222, the gap balancer 190 can be used to balance the gap, such as act 260 (FIG. 5) and FIGS. 12 and 13. The paddles 192 of the gap balancer 190 are positioned within the extension gap 224 with the trial CR femoral component 220. As the handle 194 is turned, the paddles 192 are separated one from another so that the clinician can identify a thickness of the gap and the angle between the distal femoral and the proximal tibial surfaces. Ideally, the extension gap 224 is at an angle of 0 degrees, that is, the desired rectangular gap. Unlike in the flexion gap 226, augments cannot be used to fix extension gap asymmetry as this would lead to limb malalignment. In cases of asymmetry, we attempt to balance the extension gap 224 through standard soft-tissue releases. We also check again to remove any osteophytes that may be impacting the extension gap 224 balance. Usually, with a small amount of work, the extension gap 224 can be reasonably well balanced as long as the collateral ligaments are intact.

Once the extension gap 224 is determined, the knee is then flexed to 90 degrees, and the gap balancer 190 is again tensioned, revealing a thickness and angle of the flexion gap 226, such as illustrated in FIG. 13. The flexion space symmetry is evaluated by reviewing the angle between the posterior condyles and the tibial surface. The angles provided on the gap balancer 190, in one configuration, can be in 3-degree increments. A 3 degrees misalignment can be corrected with a 5-mm augment, such as magnetic augment 222 (FIG. 11), on a large side of the gap, a 6 degrees misalignment can be corrected with 10-mm augment, such as magnetic augment 222 (FIG. 11), on the large side of the gap, and so on. If there is a degree gap between the increments provided by the gap balancer 190, such as a degree gap of about 4 or 5 degrees, the clinician can recut a portion of, for instance, a posterior condyle so that the 4-5-degree differential becomes the next closest incremental degree, such as the 5 degrees. This could include removing about 1-2 mm off of the posterior condyle, thereby converting the differential degree to a 6-degree differential which can be augmented with a 10-mm magnet augment.

If posterior augmentation is needed to either convert a trapezoidal gap to a rectangular gap or to balance the size of the extension and flexion gaps 224, 226, then magnetic augments 222 can be placed on the posterior flanges of the trial CR femur component 220, as illustrated in FIG. 13. Alternatively, or in addition to augmentation, posterior augmentation may include upsizing of the trial CR femoral component 220 to allow anterior-to-posterior fit on the femur 12.

Figure 14:
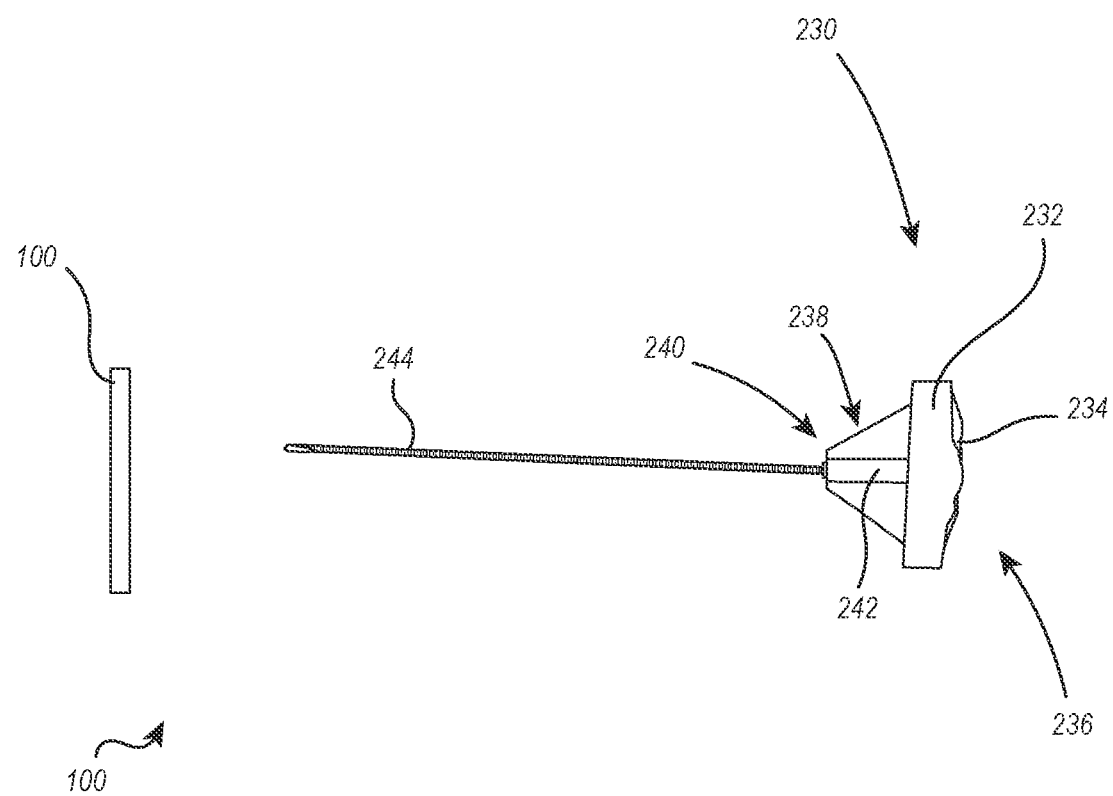
FIG. 14 illustrates a tibial component cooperating with the diameter sizing tool of FIG. 3.

Following gap balancing, a final determination of the tibial cement construct for the tibial component 230 can be performed, such as act 262 (FIG. 5). As illustrated in FIG. 14, the tibial component 230 can include a tibial body 232 with a plateau 234 at a first end 236 and a tibial keel structure 238 at a second end 240. The keel structure 238 has a plurality of keel supports 242 that form a cruciform, although other shapes are possible. For instance, the keel supports 242 can form an L-shape, T-shape, or other shapes. Additionally, the keel supports 242 can form a polygonal shape, with or with recesses therein. In addition, a single keel support rather than a plurality of keel supports 242 can form the keel structure 238, the single keel support having a cross-section that is circular, polygonal, combinations or modifications thereof. With the trial augmented CR femoral component 220 in place, the gap balancer 190 is used to recheck the extension and flexion gaps or spaces 224, 226 to assure rectangular spaces and balance of the thickness of both spaces. This gap thickness is used to determine the particular thickness of the tibial component 230.

In one configuration, it is desirable to have a flexion gap of about 1 mm to about 2 mm tighter than the extension gap 224. By so doing, the risk of flexion instability could decrease. For example, with the augmented CR femoral component 220 in place, if the extension gap 224 is rectangular and about 21 mm, and the flexion gap 226 is also rectangular and about 20 mm, then the clinician can select tibial component 230 with an overall thickness of about 21 mm. The overall thickness needed for the tibial construct equals the tibial component 230 plus the cement buildup.

With the particular flexion gap 226 and extension gap 224 identified, and the overall thickness of the tibial component 230 is selected, the tibial and femoral components 230 and 250 (FIGS. 17 and 18) and the femoral dowel 260 (FIG. 16) can be prepared for implantation, such as act 264 (FIG. 5). In the case of the femoral dowel 260, 1 or more batches of cement mixed with the appropriate amount of bacteria-specific antibiotics are prepared (forming the buildup cement) and molded around one or more Luque wires, Steinmann pins, or other structures that provide an internal support, to form a body 262 having a generally cylindrical or elongate shape with an outside diameter approximating the reamed diameter of the femoral canal. The outside diameter can be sized using the diameter sizing tool 100 by drawing or pulling the body 262 through one of the through holes 130 (FIG. 3). Alternatively, an end of the body 262 can be placed in close proximity to one of the through holes 130 (FIG. 3) to generally size the outside diameter.

In another configuration, the femoral dowel 260 can be formed using the diameter sizing tool 200 (FIG. 4). In such a case, 1 or more batches of cement mixed with the appropriate amount of bacteria-specific antibiotics is prepared and the lumen 216 (FIG. 4) is filled with the cement/antibiotic mix forming the buildup cement. The Luque wires, Steinmann pins, or other structure that can form an internal support structure for the femoral dowel, can be positioned in the buildup cement and allowed to cure, set, or otherwise solidify. Once the buildup cement has cured, set, or otherwise solidified, the elongate body 210 can be removed from the buildup cement forming the body 262 of the femoral dowel 260, such as by cutting the elongate body 210 (FIG. 4) from the body 262, sliding the elongate body 210 (FIG. 4) from the body 262, preferentially tearing or separating the elongate body 210 (FIG. 4) along the preferential cut region 220 (FIG. 4), combinations and/or modifications thereof.

For the femoral component 250, using the previously prepared buildup cement or by mixing 1 or more batches of cement with the appropriate amount of bacteria-specific antibiotics, one or more femoral augments 252 of appropriate size are molded onto a femoral component body 254, flattened to the appropriate dimensions using, for instance, an osteotome and a ruler, and allowed to harden in place.

For the tibial component 230, a stem portion or tibial keel structure 238 of the tibia component 230 can be predrilled and the Steinman pin 244 can be tapped into the tibial body 232 of the tibia component 230 just below a surface of the tibial tray or plateau 234, as illustrated in FIG. 14. Placing the pin 244 to this depth allows the tibial keel 238 to be cut off during subsequent removal procedures without hitting the pin 244.

With the pin 244 in place, using the previously prepared buildup cement or mixing 1 or more batches of cement with the appropriate amount of bacteria-specific antibiotics, the buildup cement can be placed on the tibial keel structure 238 to create tibial buildup 248 (FIG. 18) that yields a balanced knee determined by the gap thickness with the gap balancer 290 and femoral trial in place. The tibial buildup 248 can be flattened to the appropriate thickness with the aid of, for instance, the diameter sizing tool 100 (or alternatively a ruler and osteotomes). For instance, as illustrated in FIG. 14, with the pin 244 disposed through the central opening 122, the diameter sizing tool 100 can be advanced along the pin 244 until the keel structure 238 is at least partially received within the central opening 122. Continued movement of the diameter sizing tool 100 advances the upper surface 102 or the lower surface 104 to flatten and smooth the buildup cement 238 of the tibial component 230. Excess cement can pass through the through holes 130 and out from sides of the diameter sizing tool 100 and removed.

For the tibial dowel 246, the clinician can mold buildup cement around the Steinmann pin 24, or other structures that provide an internal support, to form the tibial dowel 246 having a generally cylindrical or elongate shape with an outside diameter approximating the reamed diameter of the tibial canal. The outside diameter can be sized using the diameter sizing tool 100 by drawing or pulling the tibial dowel 246 through one of the through holes 130 (FIG. 3). Alternatively, an end of the tibial dowel 246 can be placed in close proximity to one of the through holes 130 (FIG. 3) to generally size the outside diameter.

Figure 15:
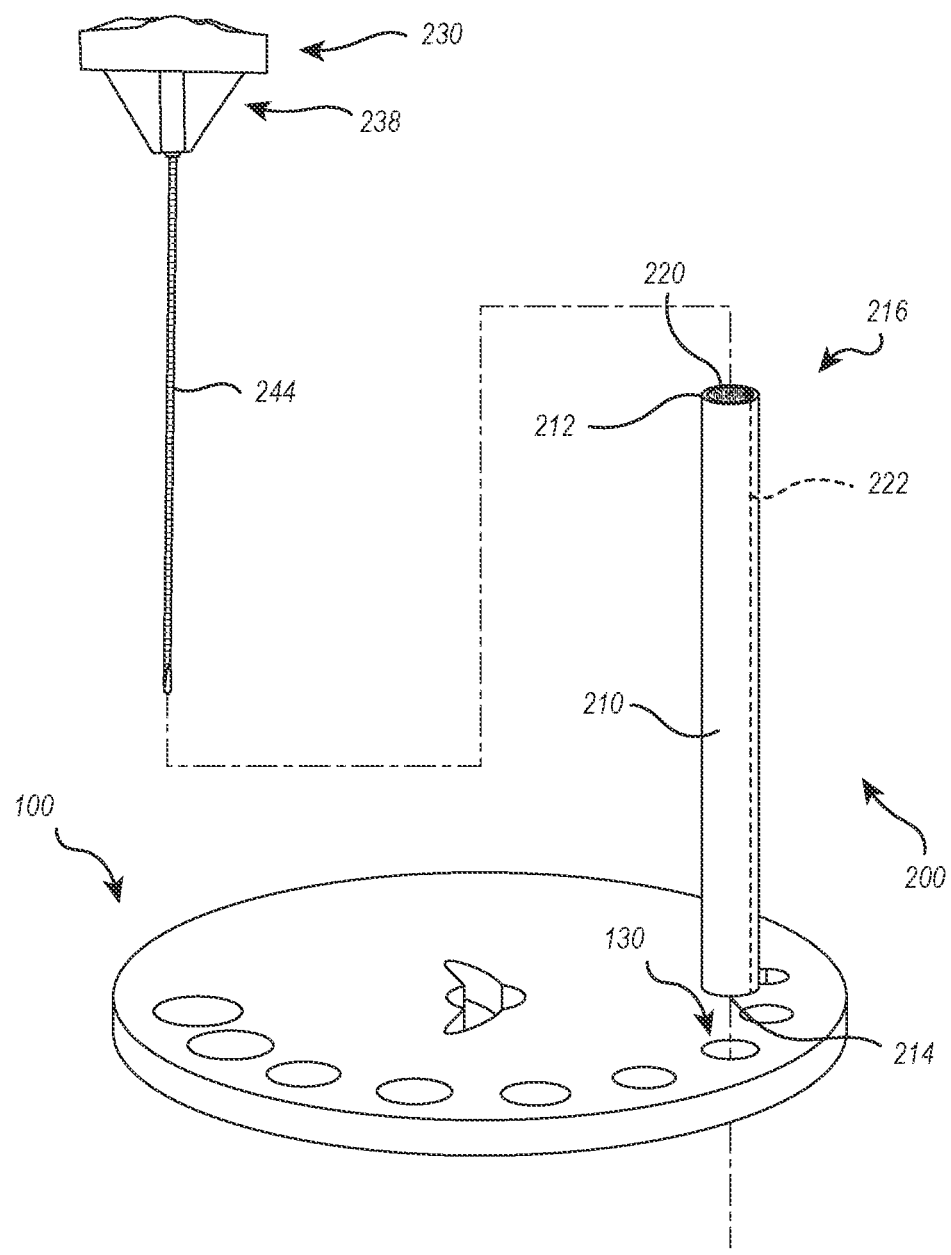
FIG. 15 illustrates a tibial component cooperating with the diameter sizing tool of FIG. 4.
Figure 16:
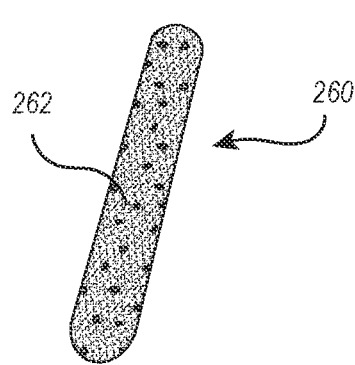
FIG. 16 illustrates a femoral dowel used as part of a total knee arthroplasty.
Figure 17:
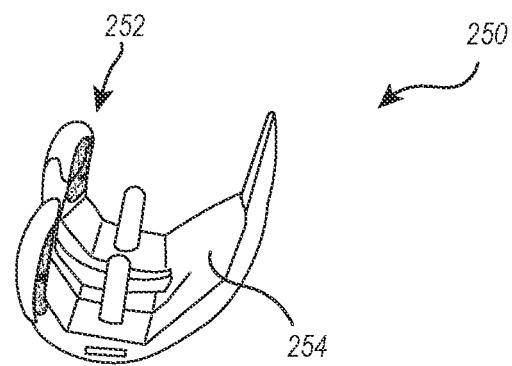
FIG. 17 illustrates a CR femoral component, with buildup augments, used as part of a total knee arthroplasty.
Figure 18:
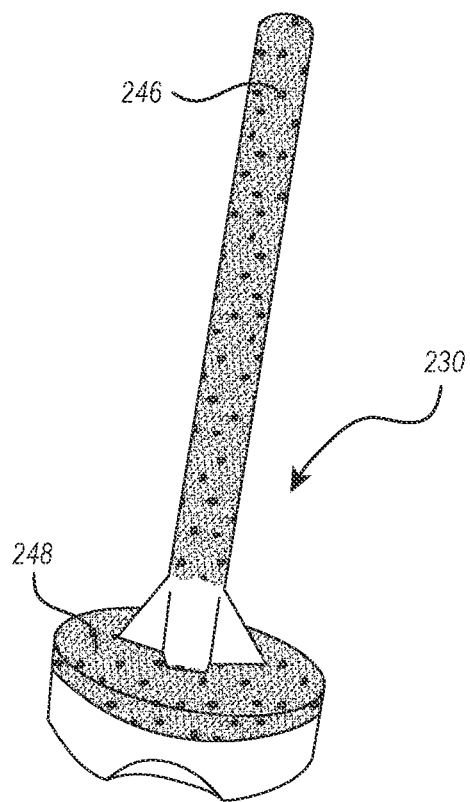
FIG. 18 illustrates a tibial component, with buildup augments, used as part of a total knee arthroplasty.
Figure 19:
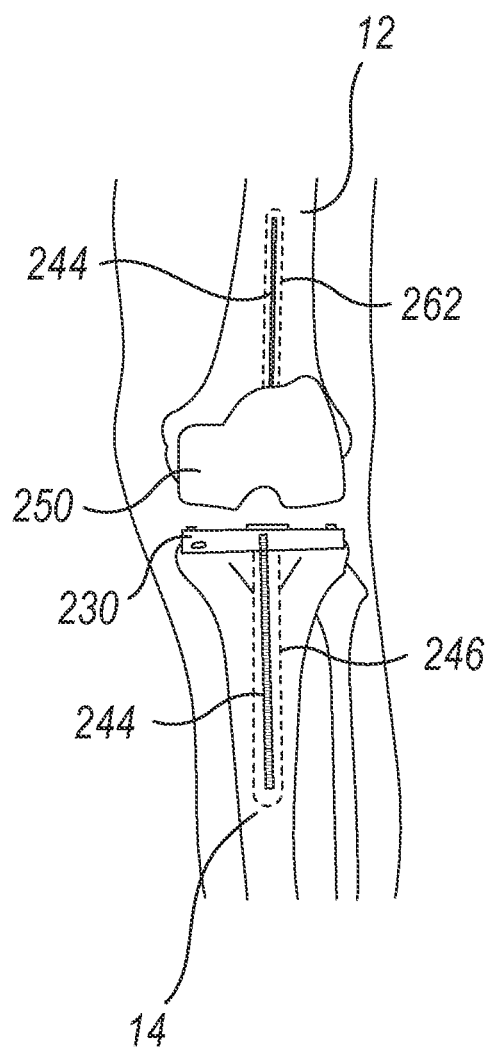
FIG. 19 illustrates the CR femoral component and the tibial component following the total knee arthroplasty.
Figure 20:
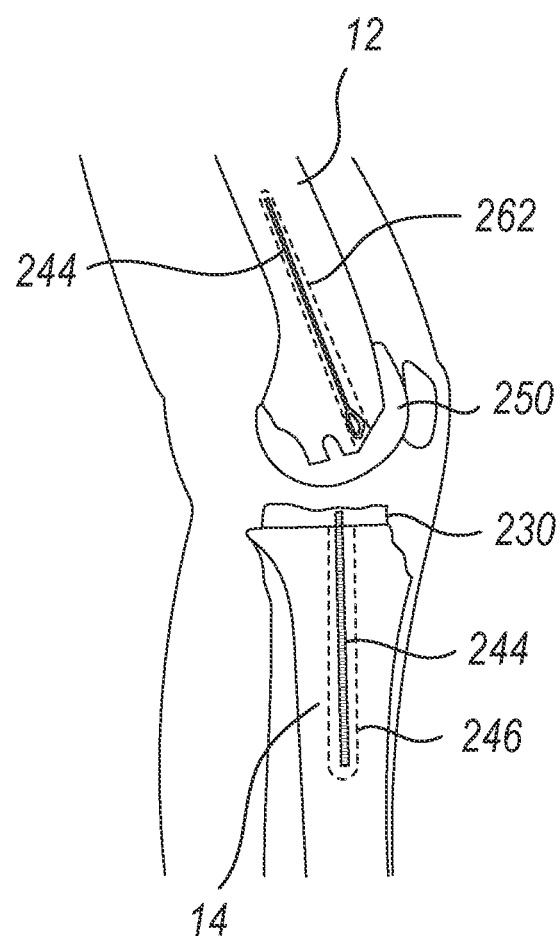
FIG. 20 illustrates a side view of the CR femoral component and the tibial component following the total knee arthroplasty.

In another configuration, the tibial dowel 246 (FIG. 8) can be formed using the diameter sizing tool 200 (FIG. 4). In such a case, the diameter sizing tool 200 can receive the Steinmann pin 244, as illustrated in FIG. 15. Using the previously prepared buildup cement and/or preparing 1 or more batches of cement mixed with the appropriate amount of bacteria-specific antibiotics the lumen 216 is filled with the cement/antibiotic mix forming the buildup cement. The buildup cement can cure, set, or otherwise solidify with the received Steinmann pin 244. Once the buildup cement has cured, set, or otherwise solidified, the elongate body 210 can be removed from the buildup cement forming the body 262 of the tibial dowel 246, such as by cutting the elongate body 210 (FIG. 4) from the body 262, sliding the elongate body 210 (FIG. 4) from the body 262, preferentially tearing or separating the elongate body 210 (FIG. 4) along the preferential cut region 220 (FIG. 4), combinations and/or modifications thereof.

As mentioned previously, during filling, or during the time when the buildup cement is setting, curing, or solidifying, the diameter sizing tool 100 can optionally be used as a support for the diameter sizing tool 200, as illustrated in FIG. 14. The first end 212 or second end 214 of the elongate body 210 can be received within one of the through holes 130 so that the diameter sizing tool 100 acts as a base or support to position the elongate body 210 of the diameter sizing tool 200 in a generally vertical orientation. The diameter sizing tool 100 can rest on a table or other surface with the elongate body 210, or diameter sizing tool 200, extending from the diameter sizing tool 100. In the case of tibial component dowel formation, the tibial component can be positioned at one end of the elongate body 210, or the diameter sizing tool 200, and the diameter sizing tool 100 at the other.

In particular, all trial components are removed, and the tourniquet is released. A thorough irrigation is performed with normal saline pulse-lavage followed by chemical debridement as per the clinician's discretion. While this irrigation and chemical debridement is taking place, the femoral component 250 and the tibia component 230 are prepared with cement augments 252, such as on a separate clean table. For instance, a stem portion or tibial keel structure 238 of the tibia component 230 can be predrilled, such as with a ¼" drill, and then a fully threaded Steinman pin 244 can be tapped into the tibial body 232 of the tibia component 230 just below to a surface of the tibial tray or plateau 234, as illustrated in FIG. 14. Placing the pin 244 to this depth allows the tibial keel 238 to be cut off during subsequent removal procedures without hitting the pin 244.

Once the dowels 246, 260 and augments 252 are hardened, additional cement and antibiotic can be prepared, such as in 2 additional batches of cement with antibiotics, and the femoral and tibial components can be implanted, such as act 266 (FIG. 5). In particular, a tourniquet can be released, and a thorough irrigation is performed with normal saline pulse-lavage followed by chemical debridement as per the clinician's discretion. Optionally, this irrigation and chemical debridement can occur during preparation of the tibial component 230, the femoral component 250, and the femoral dowel 260.

Following saline pulse-lavage and chemical debridement, the tibia component 230 can be delivered and cemented into position. The femur component 250 is positioned using an industrial retractor (not shown), and the femoral dowel 260 is placed into the femoral canal 154 (FIG. 9). The augmented femoral component 250 is then cemented into place. If there is femoral metaphyseal bone loss, the femoral metaphyseal is filed with additional cement unitizing the femoral dowel 260 to the femoral component 250, thus adding further construct stability and fixation. It is also possible to cement on a new patellar component (not shown) to reduce the possibility of patellar complications with unresurfaced techniques for articulating spacers including instability, wear, and fracture.

Using the systems, methods and devices of the present invention, a more effective first stage of the two-stage revision can be performed. In some circumstances, the methods and devices of the present invention provide patients with sufficient mobility, stability, and pain reduction that the patients could forgo the second stage of the two-stage revision. Additionally, the methods and devices of the present invention allow patients with certain femoral and tibial component material compositions, such as patients with metal-on polyethylene tibial components to bear full weight and range of the knee as tolerated as soon as soft tissues allow, thereby leading to improved patient function and satisfaction.

The diameter sizing tool and method/process described herein provide a reproducible modification of the Hofmann technique using readily available implants and instruments coupled with traditional principles of a gap-balanced revision TKA to construct a well-functioning and more durable articulating antibiotic laden spacer. The tibial and femoral components, the diameter sizing tools, and the overall method/process results in a cost-effective technique and structures as compared with other available options, demonstrates good wear characteristics, and is durable.

Again, the present invention utilizes a well-balanced articulating spacer using a cruciate-retaining (CR) femoral component and an anterior-stabilized tibial bearing tibial component. Cement augments facilitate gap balancing and cement dowels provide for increased antibiotic elution and added component fixation. The technique of the present invention yields a balanced, stable, and reasonably durable articulating antibiotic spacer that can provide patients with a well-functioning knee with the freedom of full weight-bearing and activity without feeling compelled to return to the operating room for prompt reimplantation in indicated cases.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses, are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

Following are some further example embodiments of the invention. These are presented only by way of example and are not intended to limit the scope of the invention in any way. Further, any example embodiment can be combined with one or more of the example embodiments.

Embodiment 1. A diameter sizing tool for use in reversion of total knee arthroplasty, the diameter sizing tool including a body having an upper surface, a lower surface, and a peripheral edge, a central cutout disposed through the body from the upper surface to the lower surface, and a plurality of sizing through-holes circumferentially disposed in the body and radially towards the peripheral edge.

Embodiment 2. A diameter sizing tool according to Embodiment 1, wherein a central axis of each of the plurality of sizing through-holes are disposed upon a first circumferential arc that approximates a peripheral edge of the body.

Embodiment 3. A diameter sizing tool according to any of Embodiments 1-2, wherein each of the plurality of sizing through-holes comprises an interior wall, the interior wall being perpendicular to at least one of the upper surface and the lower surface.

Embodiment 4. A diameter sizing tool according to any of Embodiments 1-3, wherein the body is formed of a polymer.

Embodiment 5. A diameter sizing tool according to any of Embodiments 1-4, further comprising indicia formed in the upper.

Embodiment 6. A diameter sizing tool according to any of Embodiments 1-5, further comprising indicial formed in a film coupled to the body.

Embodiment 7. A diameter sizing tool according to any of Embodiments 1-6, wherein a diameter of the plurality of sizing through-holes ranges from about 10 mm to about 18 mm.

Embodiment 8. A diameter sizing tool according to any of Embodiments 1-7, wherein adjacent sizing through-holes of the plurality of sizing through holes having a diameter difference of about 0.25 mm to about 1.5 mm.

Embodiment 9. A diameter sizing tool according to any of Embodiments 1-8, wherein the central cutout comprises a central opening and a first opening extension.

Embodiment 10. A method including following determination of a canal diameter, applying a cement to a tibial body of a tibial component, advancing a first diameter sizing tool over a securing pin extending from the tibial body, the securing pin extending through a hole of the diameter sizing tool, and advancing the first diameter sizing tool to contact the cement and smooth the cement.

Embodiment 11. The method of Embodiment 10, further including applying cement to the securing pin at a location for formation of a tibial dowel of the tibial component, aligning a through hole of the first diameter sizing tool with the tibial dowel, and advancing the first diameter sizing tool over the securing pin to size an outside diameter of the tibial dowel.

Embodiment 12. The method of any of Embodiments 10-11, further including forming a femoral dowel and advancing the first diameter sizing tool over the femoral dowel to size an outside diameter of the tibial dowel.

Embodiment 13. The method of any of Embodiments 10-12, wherein advancing the first diameter sizing tool to contact the cement comprises advancing the first diameter sizing tool to receive a portion of a keel structure of the tibial component within a central cutout.

Embodiment 14. The method of any of Embodiments 10-13, further including aligning a lumen of second diameter sizing tool with the securing pin and filling the lumen of the second diameter sizing tool with cement.

Embodiment 15. The method of any of Embodiments 10-14, further including removing the second diameter sizing tool from the cement following solidifying of the cement.

Embodiment 16. The method of any of Embodiments 10-15, further including removing the second diameter sizing tool further comprises cutting the second diameter sizing tool.

Embodiment 17. The method of any of Embodiments 10-16, wherein removing the second diameter sizing tool further comprises preferentially tearing the second diameter sizing tool along a preferential tear region.

Embodiment 18. The method of any of Embodiments 10-17, wherein removing the second diameter sizing tool further comprises sliding the second diameter sizing tool from the solidified cement.

Embodiment 19. A kit for use in forming an implantable dowel, the kit including a diameter sizing tool, and buildup cement configured to be used to form the implantable dowel, an outside diameter of the buildup cement being sized by the diameter sizing tool.

Embodiment 20. The kit of Embodiment 19, further including a plurality of diameter sizing tools.

Embodiment 21. The kit of any of Embodiments 19-20, wherein the diameter sizing tool includes a spacer body having an upper surface, a lower surface, and a peripheral edge; a central cutout disposed through the spacer body from the upper surface to the lower surface; and a plurality of sizing through-holes circumferentially disposed in the space body and radially towards the peripheral edge.

Embodiment 22. The kit of any of Embodiments 19-21, wherein the diameter sizing tool comprises an elongate tubular member.

Embodiment 23. The kit of any of Embodiments 19-22, wherein the elongate tubular member is formed of silicone.

Embodiment 24. The kit of any of Embodiments 19-23, wherein the diameter sizing tool comprises at least one spacer block and at least one elongate tubular member.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for use in forming an implantable dowel, the kit comprising:
    a diameter sizing tool including a plurality of sizing through-holes configured to approximate the diameter of a bone canal and to form the implantable dowel, wherein at least two sizing through-holes of the plurality of sizing through-holes have different diameters, wherein:
        the diameter sizing tool further includes a spacer body having an upper surface, a lower surface, and a peripheral edge; and
        a central cutout disposed through the spacer body from the upper surface to the lower surface,
        the plurality of sizing through-holes are circumferentially disposed in the spacer body and radially towards the peripheral edge,
        the central cutout comprises a central opening and a first opening extension and a second opening extension, wherein the first and second opening extensions curve away from the central opening along an arc; and
    buildup cement configured to be used to form the implantable dowel, an outside diameter of the buildup cement being sized by the diameter sizing tool.

2. The kit of claim 1, further comprising a plurality of diameter sizing tools.

3. The kit of claim 1, wherein the diameter sizing tool comprises an elongate tubular member and wherein the elongate tubular member is formed of silicone.

4. The kit of claim 3, wherein a sizing through-hole is configured to receive the elongate member.

5. The kit of claim 3, wherein an inner surface of the elongate tubular member comprises a coating.

6. The kit of claim 3, wherein the elongate tubular member includes a preferential cut region comprising a perforation, holes, or a thinned area configured to tear or separate.

7. The kit of claim 1, wherein the diameter sizing tool comprises at least one spacer block and at least one elongate tubular member.

8. The kit of claim 1, wherein a central axis of each of the plurality of sizing through-holes are disposed upon a first circumferential arc that approximates a peripheral edge of the body.

9. The kit of claim 1, wherein each of the plurality of sizing through-holes comprises an interior wall, the interior wall being perpendicular to at least one of the upper surface and the lower surface.

10. The kit of claim 1, wherein the body is formed from a polymer, further comprising indicia formed in the upper surface or in a film coupled to the body.

11. The kit of claim 1, wherein a diameter of the plurality of sizing through-holes ranges from about 10 mm to about 18 mm.

12. The kit of claim 1, wherein adjacent sizing through-holes of the plurality of sizing through holes having a diameter difference of about 0.25 mm to about 1.5 mm.

13. The kit of claim 1, wherein the central opening is configured to receive a tibial keel of a tibial component.

14. The kit of claim 1, wherein the upper and/or lower surface of the spacer body comprises a smooth surface.

15. The kit of claim 1, further comprising a tibia component including a tibia body and a pin.

16. The kit of claim 15, wherein the pin extends to just below a surface of a tibial tray of the tibia body.

17. A kit for use in forming an implantable dowel, the kit comprising:
    a diameter sizing tool including a plurality of sizing through-holes configured to approximate the diameter of a bone canal and to form the implantable dowel, wherein at least two sizing through-holes of the plurality of sizing through-holes have different diameters, wherein the diameter sizing tool comprises an elongate tubular member and wherein the elongate tubular member is formed of silicone, wherein the elongate tubular member includes a preferential cut region comprising a perforation, holes, or a thinned area configured to tear or separate, and
    buildup cement configured to be used to form the implantable dowel, an outside diameter of the buildup cement being sized by the diameter sizing tool.

* * * * *